United States Patent [19]

Bondi et al.

[11] Patent Number: 4,594,884

[45] Date of Patent: Jun. 17, 1986

[54] DIFFUSION MEASURING DEVICE

[75] Inventors: Joseph V. Bondi, Collegeville; Lucille A. Grabowski, Lansdale, both of Pa.

[73] Assignee: Merck & Co., Inc., Rahway, N.J.

[21] Appl. No.: 622,926

[22] Filed: Jun. 21, 1984

[51] Int. Cl.[4] ............................................. G01N 13/00
[52] U.S. Cl. .................................... 73/64.3; 210/321.2
[58] Field of Search ....................... 73/64.3; 210/321.2, 210/644, 645

[56] References Cited

U.S. PATENT DOCUMENTS 3,318,138  5/1967  Rolfson ................................. 73/64.3
3,518,875  7/1970  Charmasson .......................... 73/64.3

OTHER PUBLICATIONS

J. D. Fell et al., Use of Diaphragm Cell at Elevated Temperature, Ind. Eng. Chem. Fundam., vol. 10, No. 2, 1971.

W. Calus, M. Tyn, Three-Compartment Cell for Diffusion Measuring at Boiling Points, PAL System, 1974.

Franz, T. J., Journal of Investigative Dermatology, 64:190-195, (1975).

Anjo, D. M. et al., "Methods for Predicting Percutaneous Penetration in Man", pp. 31–43 in Percutaneous Absorption of Steroids, edited by P. Mauvais-Jarvis et al., Academic Press, 1980.

"Franz Diffusion Cells", Crown Glass Company Flyer.

"Skin Permeation Systems", flyer.

Primary Examiner—Jerry W. Myracle
Assistant Examiner—Hezron E. Williams
Attorney, Agent, or Firm—Alice O. Robertson; Michael C. Sudol

[57] ABSTRACT

A device for measuring diffusion, particularly adaptable to measuring diffusion of drugs, is described.

3 Claims, 1 Drawing Figure

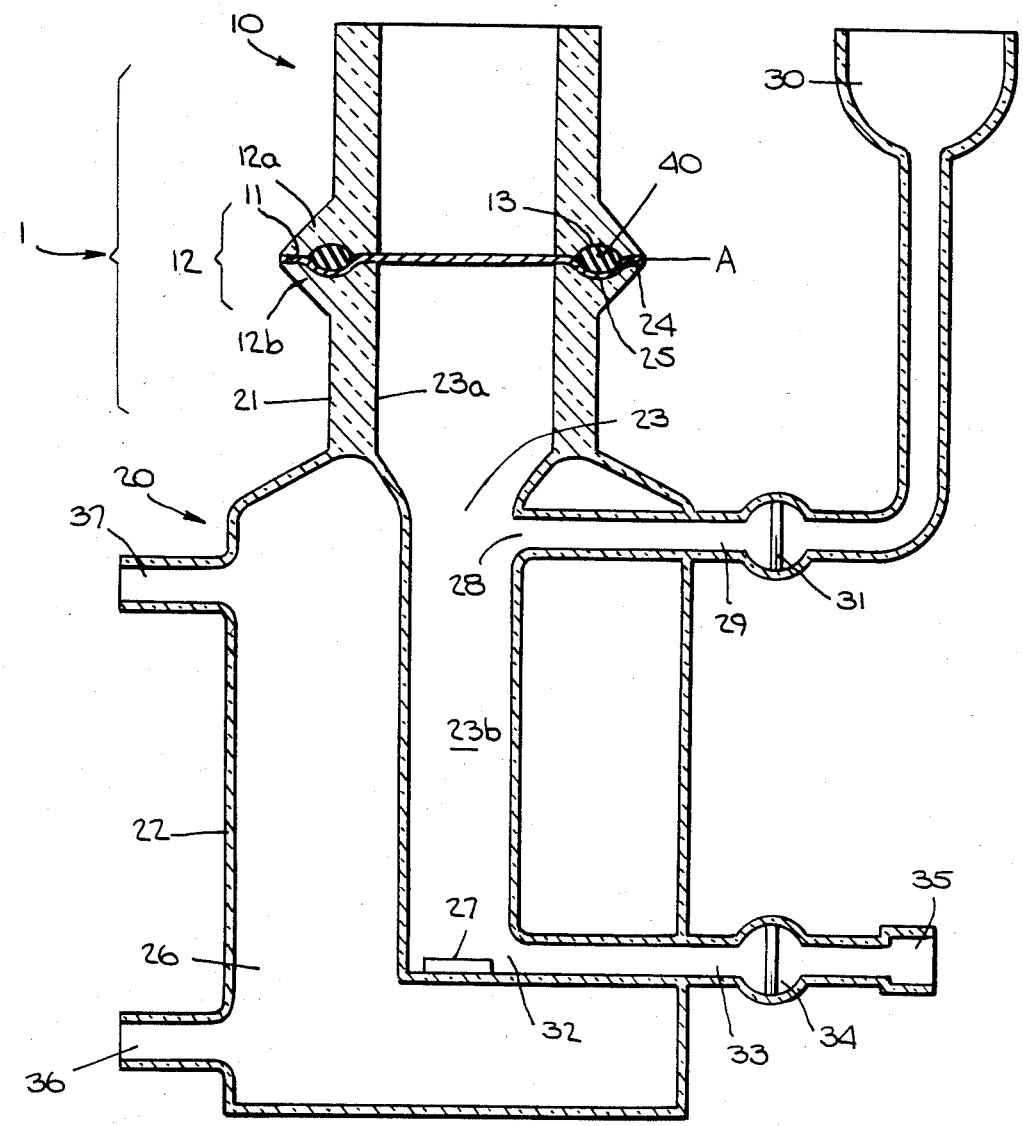

DIFFUSION MEASURING DEVICE

The present invention is concerned with a diffusion measuring device, more particularly, one adaptable to measuring diffusion of drugs.

BACKGROUND OF THE INVENTION

The effectiveness of drug applied to a skin surface is dependent on the extent of percutaneous absorption or penetration. For in vitro studies, various diffusion cells have been devised. A cell, comprising a cap, a body and 0-ring, devised by Thomas J. Franz for his study reported in J. Investigative Dermatology, 64, 190 (1975) has been adapted as a commercially available Franz diffusion cell. In this device, the body of the cell constituting the receptor chamber is that portion containing a physiological solution into which a test drug diffuses or penetrates through a test membrane which oftentimes is skin. Samples are withdrawn from the receptor chamber through a needle inserted into a sampling port constituting a side arm open to the atmosphere. The available cells have certain limitations. Thus, sample size is limited to the volume of fluid in the side arm. Moreover, when withdrawal of a large sample is attempted, there is a tendency for air to enter into the receptor chamber. Air thus introduced collects under the membrane being tested, reducing the effective surface area for drug diffusion, and thereby giving rise to erroneous measurements. It is desirable to provide for a diffusion cell which overcomes these limitations.

DESCRIPTION OF THE INVENTION

According to the present invention there is provided an apparatus for more reliably and reproducibly measuring the extent of diffusion or penetration of a test material across a test membrane, said apparatus having a variable sampling size capability, a means of maintaining the test chamber filled with solvent, and further, is not susceptible to inadvertent introduction of air into the test chamber, which comprises:

(a) a sample chamber for retaining a sample of test material to be tested for extent of diffusion or penetration through a test membrane, said chamber being opened at both ends and positioned so that the openings are in a vertical relationship, said chamber being provided at the lower end along the perimeter with a planar surface of a channeled glass joint, (b) a receptor chamber for retaining solvent or dispersing medium for the test material which diffuses or penetrates across the test membrane, said chamber being open at the upper end and closed at the lower end and being provided at its upper end along the perimeter with a planar surface of a channeled glass joint, said planar surface to complement and coact with the opposing planar surface of the sample chamber, said chamber further being jacketed for temperature control and having disposed within said chamber a covered bar magnet adaptable to being impelled when the chamber is placed on a timing motor thereby providing a stirring motion, (c) a flexible ring adaptable to being seated in the channels of the opposing faces of the glass joint and to coact with the joint surfaces to hold the test membrane in position, wherein said receptor chamber is provided with a solvent inlet port near the upper end of the chamber and a sampling outlet at the bottom of the chamber, said inlet and outlet extending substantially horizontally from the cell.

The receptor chamber comprising the body of the cell may be of a slightly larger cross-section at the upper neck-end than in the temperature-controlled main body-portion. This provides for maximum surface area for contact with the membrane while still providing a chamber of sufficiently narrow cross-section for efficient distribution of the test material in the solvent and better temperature control. The relative dimensions of the height of the chamber and the cross sectional area are dependent in part on the efficiency of mixing which in turn is dependent on the size and strength of the magnet and the power of the motor to supply the impelling action. It is a vertically elongated body with the height usually at least twice that of the width.

The receptor chamber is provided with inlet and outlet ports. The inlet port is at the upper end of the receptor chamber just below the neck portion and is provided for the purpose of supplying solvent if necessary to maintain the receptor chamber full. The arm of the solvent inlet port extends substantially horizontally away from the chamber for a short distance but thereafter extends upward to a solvent reservoir which is maintained at an elevation above that for positioning the test membrane. The arm preferably is provided with a stopcock. The outlet port extends substantially horizontally from the bottom of the receptor chamber. It is essential that the sampling outlet is at the bottom of the receptor chamber to assure that the sampling represents undiluted concentration of test material obtained during the period of the test. The horizontal tubular arm of the sampling outlet is also provided with a stopcock. In this instance, it is essential that there is a stopcock or similar closing device. The sampling arm at the end is preferably provided with a luer fitting. This permits use of medical injection syringes for sampling.

The receptor chamber is jacketed to permit temperature control by flow of water or other liquid. The temperature jacket covers the main body of the receptor chamber. The upper portion of said chamber may be of slightly larger cross-section in internal dimesions but being unjacketed, appears constricted as the neck from an external view.

The objects and advantages of this invention will be more readily apparent from the following description and accompanying drawing which illustrates the preferred embodiment of the present invention.

The FIGURE is a schematic front view of an apparatus for measuring diffusion across a test membrane.

Referring to the drawing, there is shown a diffusion measuring device 1 which comprises a sample cell 10, receptor cell 20 and a flexible ring 40.

The sample cell 10 comprises a simple cylinder, open at both ends. Circumscribing the opening at the lower end is a planar glass surface 11 constituting the surface part of one-half of a coacting fitting or joint 12a adapted to complement and coact with a similar one-half of a joint 12b of the receptor cell hereinafter described to form joint 12.

The receptor cell 20 comprises an externally visible neck 21 and body 22 and internally positioned within the neck and body, a receptor chamber 23. The receptor cell 20 is open at the top and circumscribing the opening at the upper end of the neck 21 is a planar glass surface 24 constituting the surface part of the other half of joint 12b. Both the planar surface 11 of the sample cell and the planar surface 24 of the receptor cell are grooved at a location approximately equidistant from the inner and outer edges of the planar surface forming channel 13 of the sample cell and channel 25 of the receptor cell, the channels circumscribing the opening coextensively with the planar glass surface. The dimensions of the channels are those suitable to support and encompass a flexible ring 40. The planar surface 11 and channel 13 of the sample cell 10 and the planar surface 24 and channel 25 of the receptor cell 20 coact with the flexible ring 40 with the aid of a clamp (not shown) to hold in place test membrane A.

The receptor chamber 23 of the receptor cell 20 extends from the top of the receptor cell where it constitutes the internal portion of the neck into the body 22 where it is surrounded by a jacket 26 for temperature control. The receptor chamber may contract in cross-sectional area as it extends downwardly from the neck portion 23a to the body portion 23b of said chamber. The body portion 23b constitutes the effective diffusion and mixing area. The chamber is provided with a magnet 27 encased in an inert material which lies at the bottom of the chamber and which is impelled into a stirring motion when placed in a suitable magnetic field. At the upper end of the body portion 23b of the receptor chamber is an inlet port 28, said port connected to a horizontally extending tubular arm 29 which passes through the temperature control jacket 26 to the exterior of the receptor cell and is connected to a solvent reservoir 30 maintained at an elevation above the top of the receptor cell. This is most conveniently accomplished by extending the horizontally extending tubular arm into a vertical direction and positioning a reservoir 30 at the upper end in a unitary construction. For controlling the inflow of solvent from the reservoir, a stopcock 31 is positioned in the horizontally extending tube.

At the lower end of the receptor chamber is an outlet port 32 connected to a horizontally extending tubular arm 33 which passes through the temperature control jacket 26 to the exterior. The tube is fitted with a stopcock 34 and is preferably terminated with a luer fitting 35. The luer fitting is adapted to fit a luer or medical injection syringe.

The jacket 26 totally surrounds the receptor chamber 23. The jacket is provided with an inlet 36 and outlet 37 for the temperature control liquid.

In use, a test membrane such as excised human skin, is placed across the opening of the receptor cell, the flexible ring, preferably a commonly used 0-ring, is placed over the test membrane, the sample cell placed over the receptor cell and seated over the flexible ring, and clamped into position. The material to be tested for penetration through the membrane is applied to the sample cell. The sample cell when in position for use can be likened to a cup with a penetrable bottom. The test material need not be in liquid form such as in solution. The cell is useful for any measured quantity of material. Thus, percutaneous absorption of a drug in ointment form may be determined by using excised skin for membrane and applying an ointment to the surface of the membrane on the sample cell side. The receptor cell into which the test material penetrates is filled with solvent. Typically, the cell is used for determining percutaneous absorption of drugs and for this purpose the solvent is generally a physiological buffer solution. In operation, with the test sample, e.g. a drug, the test membrane, e.g. excised skin, and the solvent, e.g. physiological buffer, in place, the instrument is placed on a suitable support for impelling spinning of the magnet stirrer 27 permitting homogeneous distribution of the permeating test material into the receptor chamber. After suitable periods of time, a sample is withdrawn from the outlet port by fitting a syringe at the luer fitting 35 and opening the stopcock 34. The volume of liquid removed is replaced through the solvent inlet port at the top of the chamber from the solvent reservoir by opening the stopcock 31 while the sample is being withdrawn.

What is claimed is:

1. An apparatus for measuring diffusion across a membrane comprising:
    (a) a sample chamber for retaining a sample of test material to be tested for extent of diffusion or penetration through a test membrane, said chamber being open at both ends and positioned so that the openings are in a vertical relationship, said chamber being provided at the lower end along the perimeter with a planar surface of a channeled glass joint,
    (b) a receptor chamber for retaining solvent or dispersing medium for the test material which diffuses or penetrates across the test membrane, said chamber being a vertical, elongated body with height at least twice that of width, being open at the upper end and closed at the lower end and being provided at its upper end along the perimeter with a planar surface of a channeled glass joint, said planar surface to complement and coact with the opposing planar surface of the sample chamber, said receptor chamber provided with a solvent inlet means near the upper end of the chamber and a sampling outlet means at the bottom edge of the chamber and further being jacketed for temperature control and having disposed within said chamber a covered bar magnet adaptable to being impelled when the chamber is on a timing motor thereby providing a stirring motion,
    (c) a flexible ring adaptable to being seated in the channels of opposing faces of the glass joint and to coact with the joint surfaces to hold the test membrane in position;
    (d) a solvent reservoir mainteined above the elevation of the test membrane, wherein the inlet means in said receptor chamber is a tubular arm extending substantially horizontally away from the chamber for a short distance and thereafter extending upward to the solvent reservoir and wherein the outlet means is a tubular arm extending substantially horizontally from the cell and fitted with a stopcock for flow control.

2. An apparatus according to claim 1 wherein the solvent inlet means is fitted with a stopcock for flow control.

3. An apparatus to claim 1 wherein the sampling outlet means has a luer fitting at the terminus of the tubular arm.

* * * * *